United States Patent
Sands et al.

(10) Patent No.: US 11,844,770 B2
(45) Date of Patent: *Dec. 19, 2023

(54) SUBSTITUTED CYCLOALKANES FOR MANAGING NEPHROGENIC DIABETES INSIPIDUS

(71) Applicant: NephroDI Therapeutics, Inc., Philadelphia, PA (US)

(72) Inventors: Jeff Sands, Atlanta, GA (US); Janet Klein, Decatur, GA (US); Ish Khanna, Alpharetta, GA (US); Sivaram Pillarisetti, Norcross, GA (US)

(73) Assignee: NephroDI Therapeutics, Inc., Seattle, WA (US)

( * ) Notice: Subject to any disclaimer, the term of this patent is extended or adjusted under 35 U.S.C. 154(b) by 114 days.

This patent is subject to a terminal disclaimer.

(21) Appl. No.: 17/506,236

(22) Filed: Oct. 20, 2021

(65) Prior Publication Data

US 2022/0031639 A1 Feb. 3, 2022

Related U.S. Application Data

(63) Continuation of application No. 16/491,990, filed as application No. PCT/US2018/016184 on Jan. 31, 2018, now Pat. No. 11,179,354.

(60) Provisional application No. 62/452,616, filed on Jan. 31, 2017.

(51) Int. Cl.
*A61K 31/19* (2006.01)
*C07C 61/00* (2006.01)
*A61K 31/16* (2006.01)
*A61P 3/10* (2006.01)
*A61K 9/00* (2006.01)
*A61K 31/194* (2006.01)
*A61K 33/00* (2006.01)

(52) U.S. Cl.
CPC ............ *A61K 31/16* (2013.01); *A61K 9/0095* (2013.01); *A61K 31/194* (2013.01); *A61K 33/00* (2013.01); *A61P 3/10* (2018.01); *A61K 9/0053* (2013.01)

(58) Field of Classification Search
CPC .............................. A61K 31/19; C07C 61/00
USPC ......................................... 514/572; 562/500
See application file for complete search history.

(56) References Cited

U.S. PATENT DOCUMENTS

| 5,864,381 | A | 1/1999 | Neal et al. |
|---|---|---|---|
| 8,623,897 | B2 | 1/2014 | Khanna et al. |
| 2004/0209847 | A1 | 10/2004 | Dasseux et al. |
| 2009/0297497 | A1 | 12/2009 | Kishore et al. |
| 2012/0071528 | A1 | 3/2012 | Khanna et al. |
| 2014/0121267 | A1 | 5/2014 | Khanna et al. |
| 2016/0367516 | A1 | 12/2016 | Sands et al. |
| 2020/0383940 | A1 | 12/2020 | Sands et al. |

FOREIGN PATENT DOCUMENTS

| WO | 2012040177 A1 | 3/2012 |
|---|---|---|
| WO | 2015002818 A1 | 1/2015 |
| WO | 2015101609 A1 | 7/2015 |

OTHER PUBLICATIONS

Dörwald, F. Zaragoza. Side Reactions in Organic Synthesis: A Guide to Successful Synthesis Design, Weinheim: Wiley-VCH Verlag GmbH & Co. KGaA, 2005, Preface.
European Extended Search Report for European Patent Application No. 18748236.9 dated Feb. 2, 2021.
International Search Report and Written Opnion for PCT/US2018/016184 dated Apr. 23, 2018.
Jordan, V. C. Nature Reviews: Drug Discovery, 2, 2003, 205.
Wang Yanhua et al.; "AMPK Stimulates Osmotic Water Permeability in Rat IMCDs", FASEB Journal, vol. 30, No. Suppl. 1, Apr. 1, 2016 (Apr. 2016), Abstract.

*Primary Examiner* — Douglas M Willis
(74) *Attorney, Agent, or Firm* — DLA Piper LLP

(57) ABSTRACT

In certain embodiments, this disclosure relates to methods of treating or preventing nephrogenic diabetes insipidus comprising administering an effective amount of 1,1'-(dodecane-1,12-diyl)bis(cyclopropane-1-carboxamide), pharmaceutical salts or derivatives thereof, as described herein, to a subject in need thereof. in certain embodiments, the subject has been diagnosed with nephrogenic diabetes insipidus.

72 Claims, 2 Drawing Sheets

SUBSTITUTED CYCLOALKANES FOR MANAGING NEPHROGENIC DIABETES INSIPIDUS

CROSS REFERENCE TO RELATED APPLICATIONS

This application is a continuation of U.S. patent application Ser. No. 16/491,990, now allowed, which claims priority to U.S. Provisional Application No. 62/452,616 filed Jan. 31, 2017 the entire disclosures of each of which are incorporated herein by this reference.

BACKGROUND

Nephrogenic diabetes insipidus (NDI) is a disease characterized by the production of large quantities of dilute urine, which results from the inability of the kidney to respond to vasopressin, the primary hormone known to enable urine concentration. Those diagnosed with NDI must consume enough fluids to equal the amount of urine produced otherwise severe dehydration may occur. Some possible outcomes of the severe dehydration include low blood pressure, delirium, or mental retardation.

Vasopressin regulates urea transport through the activation of two cyclic AMP (cAMP) dependent signaling pathways: protein kinase A (PKA) and exchange protein activated by cAMP (Epac). Vasopressin acts by increasing the phosphorylation and apical plasma membrane accumulation of the UT-A1 urea transporter protein. Vasopressin has also been shown to regulate water transport via increasing phosphorylation and apical plasma membrane accumulation of the aquaporin-2 (AQP2) water channel. Thus, the inability of the kidney to respond to vasopressin manifests itself in irregularities in urea and water transport, leading to improper urine concentration.

Metformin has been shown to improve urine concentration in rodents with NDI. Metformin has a potential side effect that it causes lactic acidosis in select cases. Thus, there is a need for improved therapeutic treatments of NDI.

Aside from lifestyle modifications that include increased water consumption and changes in diet, hydrochlorothiazide and amiloride are diuretics that manage the dehydration associated with NDI. Currently, there exist no therapies specifically targeted towards NDI. Therefore, there is a need for therapeutic treatments that address the kidney function in NDI cases.

SUMMARY

In embodiments, this disclosure relates to methods of treating or preventing nephrogenic diabetes insipidus in a subject in need thereof comprising administering a therapeutically effective amount of a compound of formula I:

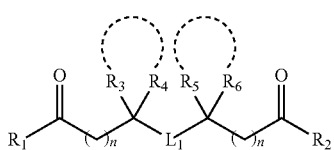

Formula I its stereoisomers or pharmaceutically acceptable salts thereof, wherein $R_1$ and $R_2$ are independently selected from a group consisting of hydroxy, alkoxy, NHR' wherein R1 is hydrogen, alkyl, cycloalkyl, SO2R or COR, wherein R is selected from alkyl or cycloalkyl; $R_3$ and $R_4$ or $R_5$ and $R_6$ are independently selected from hydrogen, or alkyl; $R_3$ and $R_4$ and/or $R_5$ and Re may form a cyclic ring of 3-5 carbon atoms; n is independently selected from 0 or 1; Li is independently a linear aliphatic chain optionally containing from 10 to 14 carbon atoms; wherein one or more symptoms of nephrogenic diabetes insipidus is treated. In embodiments, a compound of Formula I is 1,1'-(dodecane-1,12-diyl)bis(cyclopropane-1-carboxamide) (also known as NDI-5033), derivatives, prodrugs, or salts thereof In embodiments, the symptoms to be treated include the production of large quantities of dilute urine, excessive urination, and/or excessive thirst.

In embodiments, the subject is diagnosed with nephrogenic diabetes insipidus.

In embodiments, the compound of Formula I or derivative thereof is administered in combination with a cGMP-specific phosphodiesterase inhibitor, metformin, a diuretic, or a P2Y purinergic receptor antagonist.

DETAILED DESCRIPTION

Figure 1:
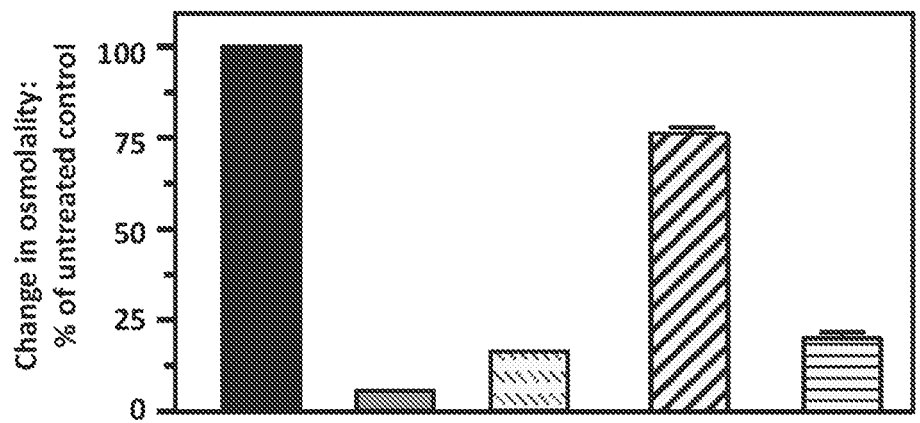
FIG. 1 shows data indicating NDI-5001, NDI-5033, and NDI-5037 improve urine concentrating ability in a rat model of NDI.

References cited herein are not an admission of prior art.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

Prior to describing the various embodiments, the following definitions are provided and should be used unless otherwise indicated. Further, headings provided herein are for convenience only and do not interpret the scope or meaning of the claims.

The compounds of the present disclosure may form one or more salts, tautomers, solvates, or contain one or more chiral centers and exist in different optically active forms. When the compound contains one chiral center, the compound comprises an enantiomer. The present disclosure includes mixtures of salts, stereoisomers, enantiomers, diastereomers, tautomers, or solvates. Enantiomers can be resolved by methods known in the art, such as crystallization, chiral chromatography and the like. When the compound contains more than one chiral centers, diastereomers may be present. The present disclosure includes specific optically pure isomers which have been resolved, as well as mixtures of diastereomers. Diastereomers can be resolved by methods known in the art, such as crystallization and preparative chromatography.

Unless the context requires otherwise, throughout the specification and claims which follow, the word "comprise" and variations thereof, such as, "comprises," "comprising" "including," "containing," or "characterized by," are to be construed in an open, inclusive sense, that is, as "including, but not limited to" and does not exclude additional, unrecited elements or method steps. By contrast, the transitional phrase "consisting of excludes any element, step, or ingredient not specified in the claim. The transitional phrase "consisting essentially of limits the scope of a claim to the specified materials or steps "and those that do not materially affect the basic and novel characteristic(s)" of the claimed invention. In embodiments or claims where the term comprising is used as the transition phrase, such embodiments can also be envisioned with replacement of the term "comprising" with the terms "consisting of" or "consisting essentially of."

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

The word "about" when immediately preceding a numerical value means a range of plus or minus 10% of that value, e.g., "about 50" means 45 to 55, "about 25,000" means 22,500 to 27,500, etc., unless the context of the disclosure indicates otherwise, or is inconsistent with such an interpretation. For example, in a list of numerical values such as "about 49, about 50, about 55, "about 50" means a range extending to less than half the interval(s) between the preceding and subsequent values, e.g., more than 49.5 to less than 52.5. Furthermore, the phrases "less than about" a value or "greater than about" a value should be understood in view of the definition of the term "about" provided herein.

The terms "administer," "administering" or "administration" as used herein refer to either directly administering a compound (also referred to as an agent of interest) or pharmaceutically acceptable salt of the compound (agent of interest) or a composition to a subject.

The term "carrier" as used herein encompasses carriers, excipients, and diluents, meaning a material, composition or vehicle, such as a liquid or solid filler, diluent, excipient, solvent or encapsulating material involved in carrying or transporting a pharmaceutical, cosmetic or other agent across a tissue layer.

As used herein, the terms "urine of the subject does not contain elevated glucose" refers to a comparison to subject with normal levels of glucose in their urine. A human subject may have glucose in urine depending on the timing, amount, and particular sugars consumed by the subject. It is normal for non-diabetics while fasting to have blood glucose levels of about 60 to 130 mg/dL. The average renal threshold is at a blood glucose level of about 160-180 mg/dL; thus, when blood glucose levels reach 160-200 mg/dL some glucose may appear in the urine. Blood sugar levels for those without diabetes and who are not fasting is typically below 160 mg/dL more than two hours after eating. A normal subject may have high blood sugar levels and glucose in urine soon after consuming a sugary drink. However, blood sugar levels after two hours of consuming a sugary drink are typically less than 200 mg/dL.

As used herein the term "lithium" refers to lithium salts typically used in the treatment of manic bipolar disorder. Examples include lithium carbonate, lithium citrate, lithium orotate, lithium bromide, and lithium chloride.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g., patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. The salts can be prepared in situ during the isolation and purification of the compounds of the disclosure, or separately by reacting the free base or free acid of a compound of the disclosure with a suitable base or acid, respectively. Examples of pharmaceutically acceptable, nontoxic acid addition salts are salts of an amino group formed with inorganic acids such as hydrochloric acid, hydro bromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkylsulfonate and aryl sulfonate.

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, adding a hydroxyl group, replacing an oxygen atom with a sulfur atom, or replacing an amino group with a hydroxyl group, oxidizing a hydroxyl group to a carbonyl group, reducing a carbonyl group to a hydroxyl group, and reducing a carb on-to-carb on double bond to an alkyl group or oxidizing a carbon-to-carbon single bond to a double bond. A derivative optional has one or more substitutions. Derivatives may be prepared by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

The terms "effective amount" and "therapeutically effective amount" are used interchangeably in this disclosure and refer to an amount of a compound that, when administered to a subject, is capable of reducing a symptom of a disorder in a subject or enhance the texture, appearance, color, sensation, or hydration of the intended tissue treatment area. The actual amount which comprises the "effective amount" or "therapeutically effective amount" will vary depending on a number of conditions including, but not limited to, the severity of the disorder, the size and health of the patient, and the route of administration. A skilled medical practitioner can readily determine the appropriate amount using methods known in the medical arts.

The phrase "pharmaceutically acceptable" or "cosmetically acceptable" is employed herein to refer to those agents of interest/compounds, salts, compositions, dosage forms, etc., which are—within the scope of sound medical judgment—suitable for use in contact with the tissues of human beings and/or other mammals without excessive toxicity, irritation, allergic response, or other problem or complication, commensurate with a reasonable benefit/risk ratio. In some aspects pharmaceutically acceptable means approved by a regulatory agency of the federal or a state government, or listed in the U.S. Pharmacopeia or other generally recognized pharmacopeia for use in mammals (e.g., animals), and more particularly, in humans.

As used herein the language "pharmaceutically acceptable excipient" is intended to include any and all carriers, solvents, diluents, excipients, adjuvants, dispersion media, coatings, antibacterial and antifungal agents, and absorption delaying agents, and the like, compatible with pharmaceutical administration.

As used herein, "pharmaceutical formulation" and "pharmaceutical composition" can be used interchangeably.

The term "patient" and "subject" are interchangeable and may be taken to mean any living organism which may be treated with compounds of the present invention. As such, the terms "patient" and "subject" may include, but is not limited to, any non-human mammal, primate or human. In some embodiments, the "patient" or "subject" is a mammal, such as mice, rats, other rodents, rabbits, dogs, cats, swine, cattle, sheep, horses, primates, or humans. In some embodiments, the patient or subject is an adult, child or infant. In some embodiments, the patient or subject is a human.

The composition may be administered to patients in an amount effective, especially to enhance pharmacological response in an animal or human organism. As used herein, the term "effective amount" refers to an amount sufficient to realize a desired biological effect. The appropriate dosage may vary depending upon known factors such as the pharmacodynamic characteristics of the particular active agent, age, health, and weight of the host organism; the condition(s) to be treated, nature and extent of symptoms, kind of concurrent treatment, frequency of treatment, the need for prevention or therapy and/or the effect desired. The dosage will also be calculated dependent upon the particular route of administration selected. Further refinement of the calculations necessary to determine the appropriate dosage for treatment is routinely made by a practitioner, in the light of the relevant circumstances. The titer may be determined by conventional techniques.

As used herein, the term "AMPK activator" refers to a substance that activates adenosine monophosphate kinase, AMPK.

A "linking group" refers to any variety of molecular arrangements that can be used to bridge two molecular moieties together.

As used herein, "alkyl" means a noncyclic straight chain or branched, unsaturated or saturated hydrocarbon such as those containing from 1 to 10 carbon atoms. A "higher alkyl" refers to unsaturated or saturated hydrocarbon having 6 or more carbon atoms. A "C8-C18" refers to an alkyl containing 8 to 18 carbon atoms. Likewise a "C6-C22" refers to an alkyl containing 6 to 22 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

The term "aryl" refers to aromatic homocyclic (i.e., hydrocarbon) mono-, bi- or tricyclic ring-containing groups preferably having 6 to 12 members such as phenyl, naphthyl and biphenyl. Phenyl is a preferred aryl group.

"Alkoxy" refers to an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, propoxy, n-butoxy, s-butoxy, t-butoxy.

"Alkoxyalkyl" refers an alkyl group as defined above with the indicated number of carbon atoms attached through an alkyl bridge (i.e., —CH2-O—CH2CH3).

The terms "cycloalkyl" and "cycloalkenyl" refer to mono-, bi-, or tri-homocyclic ring groups of 3 to 15 carbon atoms which are, respectively, fully saturated and partially unsaturated.

The term "substituted" refers to a molecule wherein at least one hydrogen atom is replaced with a substituent. When substituted, one or more of the groups are "substituents." The molecule may be multiply substituted.

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis. Typical prodrugs are pharmaceutically acceptable esters. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like.

By way of example only, appropriate prodrugs can be prepared by reacting a non-derivatized compound with a suitable carbamylating agent, such as, but not limited to, 1,1-acyloxyalkylcarbanochloridate, paranitrophenyl carbonate, or the like. Prodrug forms of the herein described compounds, wherein the prodrug is metabolized in vivo to produce a derivative as set forth herein are included within the scope of the claims.

Pharmaceutically acceptable prodrugs of the compounds described herein also include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters. Compounds having free amino, amino, hydroxy or carboxylic groups can be converted into prodrugs. For instance, free carboxyl groups can be derivatized as amides or alkyl esters. In certain instances, all of these prodrug moieties incorporate groups including but not limited to ether, amine and carboxylic acid functionalities.

In some embodiments, prodrugs include compounds wherein an amino acid residue, or a polypeptide chain of two or more (e. g., two, three or four) amino acid residues is covalently joined through an amide or ester bond to a free amino, hydroxy or carboxylic acid group of compounds of the present disclosure. The amino acid residues include but are not limited to the 20 naturally occurring amino acids and also includes 4-hydroxyproline, hydroxylysine, demosine, isodemosine, 3-methylhistidine, norvaline, beta-alanine, gamma-aminobutyric acid, cirtulline, homocysteine, homoserine, ornithine and methionine sulfone.

For example, if a disclosed compound or a pharmaceutically acceptable form of the compound contains a carboxylic acid functional group, a prodrug can comprise a pharmaceutically acceptable ester formed by the replacement of the hydrogen atom of the acid group with a group such as (C1-C8)alkyl, (C2-Ci2)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxy carbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)amino) ethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N—(C1-C2)-alkylamino-(C2-C3)alkyl (such as beta-dimethylaminoethyl), carbamoyl-(C1-C2)alkyl, N,N-di(C1-C2)-alkylcarbamoyl-(C1-C2)alkyl and piperidino-, pyrrolidino- or morpholino-(C2-C3)alkyl.

If a disclosed compound or a pharmaceutically acceptable form of the compound contains an alcohol functional group, a prodrug can be formed by the replacement of the hydrogen atom of the alcohol group with a group such as (C1-C6) alkanoyloxymethyl, 1-((C1-C6)alkanoyloxy) ethyl, 1-methyl-1((C1-C6)alkanoyloxy)ethyl(C1-C6)alkoxy carbonyl oxymethyl, N—(C1-C6)-alkoxycarbonylaminomethyl, succinoyl, (C1-C6)alkanoyl, alpha-amino(C1-C4)alkanoyl, arylaoyl and alpha-aminoacyl, or alpha-aminoacyl-alpha-aminoacyl, where each alpha-aminoacyl group is independently selected from naturally occurring L-amino acids, P(O)(OH)2, —P(O)(O(C1-C6)alkyl)2, and glycosyl (the radical resulting from the removal of a hydroxyl group of the hemiacetal form of a carbohydrate).

If a disclosed compound or a pharmaceutically acceptable form of the compound incorporates an amine functional group, a prodrug can be formed by the replacement of a hydrogen atom in the amine group with a group such as R-carbonyl, RO-carbonyl, NRR'-carbonyl where R and R' are each independently (C1-C6)alkyl, (C3-C7)cycloalkyl, benzyl, a natural alpha-aminoacyl, —C(OH)C(O)OYi wherein $Y^1$ is H, (C1-C6)alkyl or benzyl, —C(OY2)Y3 wherein Y2 is (C1-C4) alkyl and Y3 is (C1-C6)alkyl, carboxy(C1-C6)alkyl, amino(C1-C4)alkyl or di-N,N-(Ci-C6)alkylaminoalkyl, —C(Y4)Y5 wherein Y4 is H or methyl and Y5 is mono-N— or di-N,N—(C1-C6)alkylamino, morpholino, piperidinalkyl or pyrrolidinalkyl.

Embodiments of the invention are directed to methods of treating or preventing a condition in a subject in need thereof comprises administering a therapeutically effective amount of a compound of formula I as described herein.

In embodiments, the condition to be treated is characterized by the production of large quantities of dilute urine, excessive urination, and/or excessive thirst. In embodiments, the subject is treated and does not produce large quantities of dilute urine. In embodiments, when the subject is treated by the administration of the compound of Formula I, the subject does not experience excessive urination. In embodiments, when the subject is treated by the administration of the compound of Formula I, the subject does not experience excessive thirst. In embodiments, when the subject is treated by administration of the compound of Formula I, the urine of the subject does not contain elevated glucose.

In embodiments, when the subject is treated by the administration of the compound of formula I, it does not alter blood sugar levels, it does not induce hypoglycemia in a fasting condition, and/or the urine of the subject does not contain elevated glucose. In embodiments, when the subject is treated by the administration of the compound of Formula I, the subject does not experience gastrointestinal distress.

In embodiments, the condition is nephrogenic diabetes insipidus (NDI). In embodiments, the subject has been diagnosed with NDI using a test where the subject is restricted from drinking water and the hourly increase in osmolality of urine of the subject is less than 30 mOsm/kg per hour for at least 3 hours. Nephrogenic diabetes insipidus (NDI), a form of diabetes insipidus, is a disease characterized by the production of large quantities of dilute urine, which results from the inability of the kidney to respond to vasopressin, the primary hormone known to enable urine concentration. To avoid dehydration, those diagnosed with NDI must consume enough fluids to equal the amount of urine produced, which may be as high as 20 L of water per day. A symptom of NDI is the production of large quantities of dilute urine. The concentration of urine, or how dilute a subject's urine is, as measured by the osmolality of the urine. In severe cases of NDI the subject's urine concentration is less than 100 mOsm/kg. In mild cases of NDI the subject's urine concentration is less than 150 mOsm/kg. In embodiments, the subject is treated and the osmolality of the urine is greater than 100 mOsm/kg, greater than 110 mOsm/kg, greater than 120 mOsm/kg, greater than 130 mOsm/kg, greater than 140 mOsm/kg, greater than 150 mOsm/kg, greater than 160 mOsm/kg, greater than 170 mOsm/kg, greater than 180 mOsm/kg, greater than 190 mOsm/kg, or greater than 200 mOsm/kg. In embodiments, the subject is treated and daily urine osmolality is increased by about 50% per day, increased by about 40% per day, increased by about 30% per day, or increased by about 20% per day. In severe cases of NDI the subject produces as much as or greater than 20 L of urine per day. In mild cases of NDI the subject produces greater than 5 L of urine per day. In embodiments, the symptom of excessive urination is treated, and the amount of urine produced is less than 20 L/day, less than 19 L/day, less than 18 L/day, less than 17 L/day, less than 16 L/day, less than 15 L/day, less than 14 L/day, less than 13 L/day, less than 12 L/day, less than 11 L/day, less than 10 L/day, less than 9 L/day, less than 8 L/day, less than 7 L/day, less than 6 L/day, less than 5 L/day, less than 4 L/day, less than 3 L/day, less than 2 L/day, or less than 1 L/day. In embodiments, the subject experiences a reduction in the daily volume of urination selected from the group consisting of reducing the daily volume of urination by 5%, reducing the daily volume of urination by 10%, reducing the daily volume of urination by 15%, reducing the daily volume of urination by 20%, reducing the daily volume of urination by 25%, reducing the daily volume of urination by 30%, reducing the daily volume of urination by 35%, reducing the daily volume of urination by 40%, reducing the daily volume of urination by 45%, reducing the daily volume of urination by 50%. In embodiments, the subject experiences a reduction in the daily frequency of urination selected from the group consisting of reducing the daily frequency of urination by 5%, reducing the daily frequency of urination by 10%, reducing the daily frequency of urination by 15%, reducing the daily frequency of urination by 20%, reducing the daily frequency of urination by 25%, reducing the daily frequency of urination by 30%, reducing the daily frequency of urination by 35%, reducing the daily frequency of urination by 40%, reducing the daily frequency of urination by 45%, reducing the daily frequency of urination by 50%.

In embodiments, the condition is acquired NDI. Acquired NDI is most commonly thought to stem from chronic lithium treatment, a classic treatment for bipolar disorders. Those undergoing chronic lithium treatment display no mutations in either the UT-A1 or AQP2 proteins. Thus, it is the inability to respond to vasopressin, and subsequently undergo phosphorylation of UT-A1 and AQP2, that leads to defects in urine concentration. In embodiments, nephrogenic diabetes insipidus is prevented or severity reduced in a subject being treated with lithium for a psychiatric disorder, wherein the subject is administered a therapeutically effective amount of lithium in combination with a therapeutically effective amount of a compound of Formula I or derivative thereof as described herein. In certain embodiments, the subject is diagnosed with a psychiatric disorder such as major depressive disorder, manic episodes, or bipolar disorder. In embodiments, a therapeutically effective amount of compound of Formula I is administered to a subject to treat nephrogenic diabetes insipidus induced by lithium therapy.

In embodiments, the condition is congenital NDI. Congenital NDI arises from mutations in the vasopressin receptor, V2R, causing it to malfunction, or in the kidney water channel AQP2, resulting in a decreased ability to absorb water. Those possessing V2R mutations display no mutations in either the UT-A1 or AQP2 proteins. Thus, it is the inability to respond to vasopressin, and subsequently undergo phosphorylation, that leads to defects in urine concentration.

Embodiments of the invention are directed to methods of treating or preventing acquired NDI in a subject in need thereof comprises administering a therapeutically effective amount of a compound of Formula I as described herein. In embodiments, the subject is being administered lithium. In embodiments, the subject is being administered lithium and is at risk of developing acquired NDI or has developed acquired NDI. In embodiments, the subject is diagnosed with a psychiatric disorder and the subject is administered a therapeutically effective amount of lithium. In certain embodiments, the subject is diagnosed with a psychiatric disorder such as major depressive disorder, manic episodes, or bipolar disorder. In embodiments, the lithium is administered in combination with a therapeutically effective amount compound of Formula I or derivative thereof as described herein to prevent development of or treat NDI. In embodiments, the lithium and the compound of Formula I or derivative thereof as described herein are administered in a single pharmaceutical composition or in separate pharmaceutical compositions.

In embodiments, the subject is an adult. In embodiments, the subject is a non-adult or a child.

In embodiments, the class of compounds are classified as AMPK activators, since they enable the phosphorylation of both the UT-A1 and AQP2 proteins.

In embodiments, the compound of Formula I are compounds of Formula I,

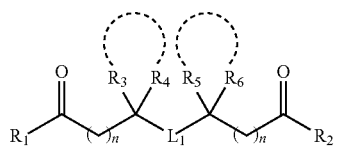

Formula I its stereoisomers or pharmaceutically acceptable salts thereof, wherein R1 and R2 are independently selected from a group consisting of hydroxy, alkoxy, NHR' wherein R' is hydrogen, alkyl, cycloalkyl, SO2R or COR, wherein R is selected from alkyl or cycloalkyl; R3 and R4 or R5 and R6 are independently selected from hydrogen, or alkyl; R3 and R4 and/or R5 and R6 may form a cyclic ring of 3-5 carbon atoms; n is independently selected from 0 or 1; Li is independently a linear aliphatic chain optionally containing from 10 to 14 carbon atoms. In embodiments, at least one of R3 and R4 and/or R5 and R6 forms a cyclic ring of 3-5 carbon atoms, R3 and R4 or R5 and R6.

In embodiments, the compound of formula I are compounds of formula IA,

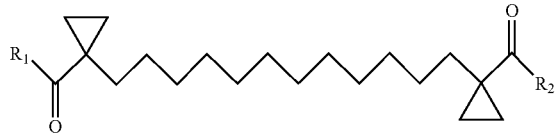

Formula IA its stereoisomers or pharmaceutically acceptable salts thereof, wherein R1 and R2 are independently selected from a group consisting of hydroxyl, alkoxy, or NHR' wherein R' is hydrogen, alkyl, or cycloalkyl.

In embodiments, the compound of Formula I is 1,1'-(dodecane-1,12-diyl)bis(cyclopropane-1-carboxamide) or derivatives or salts thereof. This compound is also referred to as NDI-5033 and is depicted as having the following structure:

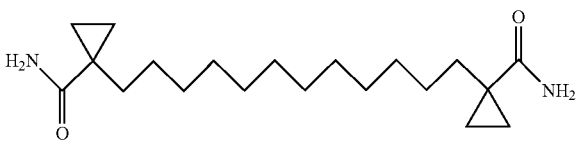 [SMILES: NC(=O)C1(CCCCCCCCCCCCC2(C(N)=O)CC2)CC1]

In embodiments, the compound of Formula I is 1,1'-(decane-1,10-diyl)bis(cyclopropane-1-carboxylic acid) or derivatives or salts thereof. This compound is also referred to as NDI-5001 and is depicted as having the following structure:

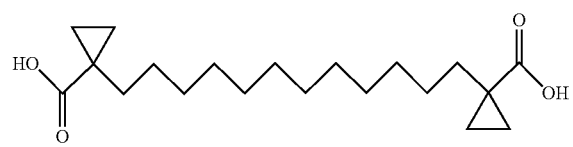 [SMILES: O=C(O)C1(CCCCCCCCCCCCC2(C(=O)O)CC2)CC1]

In embodiments, the compound of Formula I is 1-(10-(1-(cyclopropylcarbarnoyl)cyclopropyl)decyl)cyclopropane-1-carboxylic acid or derivatives or salts thereof. This compound is also referred to as NDI-5037 and is depicted as having the following structure:

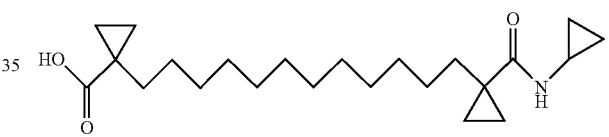

In certain embodiments, a compound of Formula I include the following examples. The preparation of these examples are provided for in US Patent Publications 20140121267 and 20120071528.

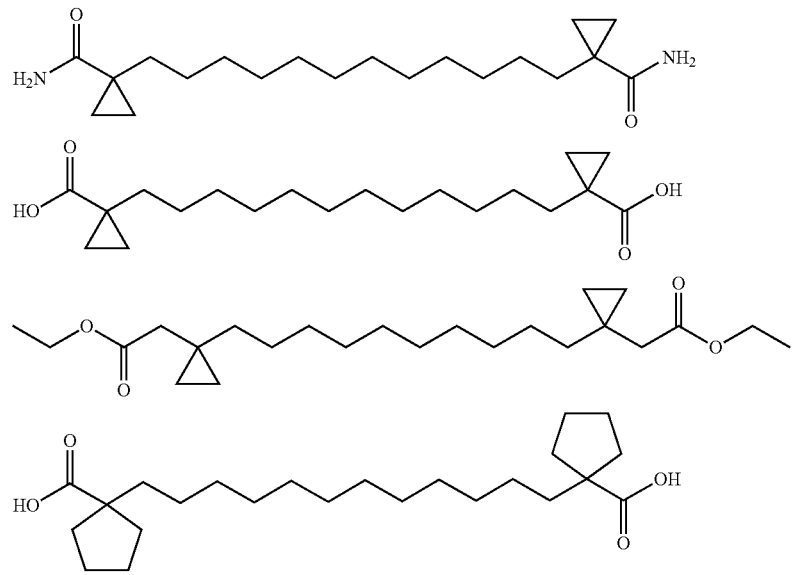

-continued

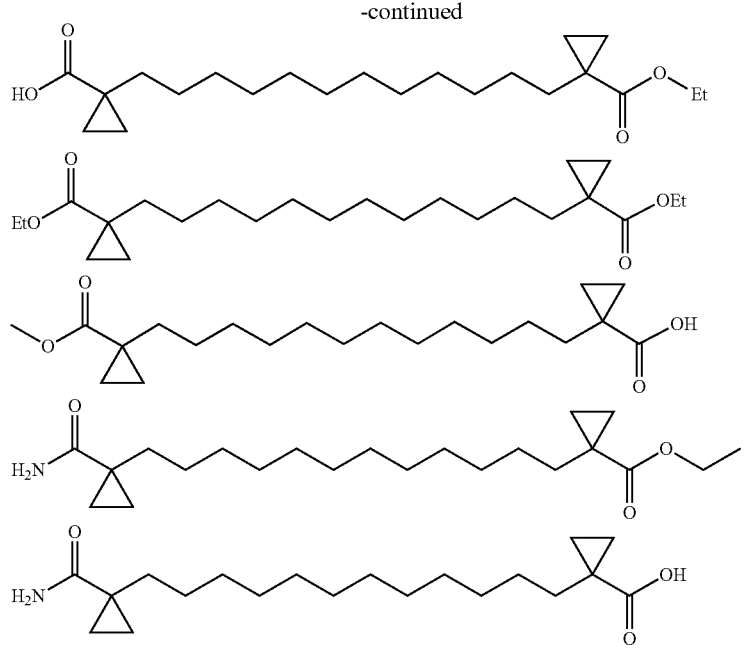

In embodiments, the therapeutically effective amount of a compound of Formula I may be from about 0.1 mg/day to about 3,000 mg/day. In embodiments, the therapeutically effective amount of a compound of Formula I may be from about 0.1 mg/day to about 2,000 mg/day. In embodiments, the therapeutically effective amount of a compound of Formula I may be from about 0.1 mg/day to about 800 mg/day. In embodiments, the therapeutically effective amount of a compound of Formula I may be from about 0.1 mg/day to about 500 mg/day. In embodiments, the therapeutically effective amount of a compound of Formula I may be from about 0.1 mg/day to about 250 mg/day. In embodiments, the therapeutically effective amount of a compound of Formula I may be from about 1 mg/day to about 1,000 mg/day. In embodiments, the therapeutically effective amount of a compound of Formula I may be from about 1 mg/day to about 750 mg/day. In embodiments, the therapeutically effective amount of a compound of Formula I may be from about 1 mg/day to about 500 mg/day. In embodiments, the therapeutically effective amount of a compound of Formula I may be from about 1 mg/day to about 300 mg/day. In embodiments, the therapeutically effective amount of a compound of Formula I may be from about 1 mg/day to about 200 mg/day. In embodiments, the therapeutically effective amount of a compound of Formula I may be from about 10 mg/day to about 3,000 mg/day.

In embodiments, the therapeutically effective amount of a compound of Formula I for an adult subject may be from about 5 mg to about 1,000 mg per day. In embodiments, the therapeutically effective amount of a compound of Formula I for an adult subject may be from about 20 mg to about 750 mg per day. In embodiments, the therapeutically effective amount of a compound of Formula I for an adult subject may be from about 50 mg to about 800 mg per day. In embodiments, the therapeutically effective amount of a compound of Formula I for an adult subject may be from about 60 mg to about 750 mg per day. In embodiments, the therapeutically effective amount of a compound of Formula I for an adult subject may be from about 70 mg to about 750 mg per day. In embodiments, the therapeutically effective amount of a compound of Formula I for an adult subject may be from about 80 mg to about 750 mg per day. In embodiments, the therapeutically effective amount of a compound of Formula I for an adult subject may be from about 90 mg to about 500 mg per day. In embodiments, the therapeutically effective amount of a compound of Formula I for an adult subject may be from about 100 mg to about 450 mg per day. In embodiments, the therapeutically effective amount of a compound of Formula I for an adult subject may be from about 110 mg to about 400 mg per day. In embodiments, the therapeutically effective amount of a compound of Formula I for an adult subject may be from about 120 mg to about 350 mg per day. In embodiments, the therapeutically effective amount of a compound of Formula I for an adult subject may be from about 130 mg to about 300 mg per day. In embodiments, the therapeutically effective amount of a compound of Formula I for an adult subject may be from about 140 mg to about 250 mg per day. In embodiments, the therapeutically effective amount of a compound of Formula I for an adult subject may be from about 150 mg to about 200 mg per day. In embodiments, the therapeutically effective amount of a compound of Formula I for a non-adult subject may be from about 0.1 mg to about 500 mg per day. In embodiments, the therapeutically effective amount of a compound of Formula I for a non-adult subject may be from about 1 mg to about 450 mg per day. In embodiments, the therapeutically effective amount of a compound of Formula I for a non-adult subject may be from about 5 mg to about 400 mg per day. In embodiments, the therapeutically effective amount of a compound of Formula I for a non-adult subject may be from about 10 mg to about 350 mg per day. In embodiments, the therapeutically effective amount of a compound of Formula I for a non-adult subject may be from about 15 mg to about 300 mg per day. In embodiments, the therapeutically effective amount of a compound of Formula I for a non-adult subject may be from about 20 mg to about 250 mg per day. In embodiments, the therapeutically effective amount of a compound of Formula I for a non-adult subject may be from about 25 mg to about 200 mg per day. In embodiments, the therapeutically effective amount of a compound of Formula I for a non-adult subject may be from about 30 mg to about 150 mg per day. In embodiments, the therapeutically effective amount of a compound of Formula I for a non-adult subject may be from about 50 mg to about 100 mg per day.

In embodiments, for the administrations disclosed herein similar amounts converted to molar equivalents of the salts are contemplated. In embodiments, administrations may include an amount of less than 5%, 10%, or 20% variation by weight.

In embodiments, the therapeutically effective amount of a compound of Formula I may be administered in a single dose or a dose repeated one or several times after a certain time interval. In embodiments, the therapeutically effective amount is administered daily or every two or three days, or once a week. Administration may be one, twice, or three times daily, e.g., single dose of 500 mg daily, single dose of 850 mg, 850 mg twice daily, or 850 my three times daily, single dose of 1,000 mg daily, single dose of 100 mg daily, single dose of 200 mg, single dose of 400 mg, 100 mg twice daily, or 200 mg three times daily. In embodiments, the therapeutically effective amount is administered daily or every other day for more than two weeks, ten weeks, thirty weeks, a year, or as long as symptoms or the disease are present. In embodiments, the therapeutically effective amount is administered daily or every other day for more than thirty weeks.

In embodiments, the compound of Formula I may be administered systemically or locally. For example, administration can be, but is not limited to, parenteral, subcutaneous, intravenous, intramuscular, intraperitoneal, transdermal, oral, buccal, intranasally, intravaginally, by inhalation, by depot injections, or by implants. In embodiments, the compound of Formula I is suitable for oral administration. In embodiments, the compound of Formula I is administered in the form of a pill, tablet, capsule, gel, gummy, liquid, or in the form of an aqueous saline buffer. In embodiments, the pharmaceutically acceptable excipient is a saccharide or polysaccharide.

In embodiments, the compound of Formula I is in a pharmaceutical composition. In embodiments, a pharmaceutical composition of the disclosure comprises a carrier and/or diluent appropriate for its delivering by injection to a human or animal organism. Such carrier and/or diluent is non-toxic at the dosage and concentration employed. It is selected from those usually employed to formulate compositions for parental administration in either unit dosage or multi-dose form or for direct infusion by continuous or periodic fusion. It is typically isotonic, hypotonic or weakly hypertonic and has a relatively low ionic strength, such as provided by sugars, polyalcohols and isotonic saline solutions. Representative examples include sterile water, physiological saline (e.g. sodium chloride), bacteriostatic water, Ringer's solution, glucose or saccharose solution, Hank's solution, and other aqueous physiologically balanced salt solutions (see for example the most current editions of Remington: The Science and Practice of Pharmacy, A. Gennaro, Lippincott, Williams & Wilkins). The pH of the composition of the disclosure is suitably adjusted and buffered in order to be appropriate for use in humans or animals, typically at a physiological or slightly basic pH (between about pH 8 to about pH 9, with a special preference for pH 8.5). Suitable buffers include phosphate buffer (e.g. PBS), bicarbonate buffer and/or Tris buffer. A typical composition is formulated in 1M saccharose, 150 mM NaCl, 1 mM MgCl2, 54 mg/l Tween 80, 10 mM Tris pH 8.5. Another typical composition is formulated in 10 mg/ml mannitol, 1 mg/ml HAS, 20 mM Tris, pH 7.2, and 150 mM NaCl.

The pharmaceutical composition of the disclosure can be in various forms, e.g. in solid (e.g. powder, lyophilized form), or liquid (e.g. aqueous). In the case of solid compositions, the typical methods of preparation are vacuum drying and freeze-drying which yields a powder of the active agent plus any additional desired ingredient from a previously sterile-filtered solution thereof. Such solutions can, if desired, be stored in a sterile ampoule ready for reconstitution by the addition of sterile water for ready injection.

Nebulized or aerosolized formulations also form part of this disclosure. Methods of intranasal administration include the administration of a droplet, spray, or dry powdered form of the composition into the nasopharynx of the individual to be treated from a pressured container or dispenser which contains a suitable propellant, e.g., a gas such as carbon dioxide, or a nebulizer (see for example WO 95/11664). Enteric formulations such as gastroresistant capsules and granules for oral administration, suppositories for rectal or vaginal administration also form part of this disclosure. For non-parental administration, the compositions can also include absorption enhancers which increase the pore size of the mucosal membrane. Such absorption enhancers include sodium deoxy cholate, sodium glycocholate, dimethyl-beta-cyclodextrin, lauroyl-1-lysophosphatidylcholine and other substances having structural similarities to the phospholipid domains of the mucosal membrane.

The pharmaceutical composition can also contain other pharmaceutically acceptable excipients for providing desirable pharmaceutical or pharmacodynamic properties, including for example modifying or maintaining the pH, osmolarity, viscosity, clarity, color, sterility, stability, rate of dissolution of the formulation, modifying or maintaining release or absorption into an the human or animal organism. For example, polymers such as polyethylene glycol may be used to obtain desirable properties of solubility, stability, half-life and other pharmaceutically advantageous properties (Davis et al., 1978, Enzyme Eng. 4, 169-173; Burnham et al., 1994, Am. J. Hosp. Pharm 51, 210-218). Representative examples of stabilizing components include polysorbate 80, Larginine, polyvinylpyrrolidone, trehalose, and combinations thereof. Viscosity enhancing agents include sodium carboxymethylcellulose, sorbitol, and dextran. The composition can also contain substances known in the art to promote penetration or transport across the blood barrier or membrane of a particular organ (e.g. antibody to transferrin receptor; Friden et al., 1993, Science 259, 373-377). A gel complex of poly-lysine and lactose (Midoux et al., 1993, Nucleic Acid Res. 21, 871-878) or poloxamer 407 (Pastore, 1994, Circulation 90, 1-517) can be used to facilitate administration in arterial cells.

In embodiments, the methods may include the co-administration of a second active agent. In embodiments, co-administration may be part of the same pharmaceutical composition or separated pharmaceutical compositions described herein. In embodiments, co-administration may be at the same time, substantially the same time, before or after administration of the compositions described herein.

In embodiments, the second active agent may be selected from the group consisting of a cGMP-specific phosphodiesterase inhibitor, an AMPK activator, a diuretic, a P2Y purinergic receptor antagonist, and lithium.

In embodiments, lithium is administered in an amount selected from the group consisting of 150 mg, 300 mg, 450 mg, and 600 mg.

In embodiments, the cGMP-specific phosphodiesterase inhibitor is selected from the group consisting of sildenafil, vardenafil, tadalafil, and avanafil.

In embodiments, the AMPK activator is selected from the group consisting of metformin, Proguanil, cryptotanshinone, 5-aminoimidazole-4-carboxamide-1-beta-D-ribofuranoside, A-769662 [4-hydroxy-3-(2'-hydroxy-[1,1'-biphenyl]-4-yl)-6-oxo-6,7-dihydrothieno[2,3-b]pyridine-5-carbonitrile], D942 [5-(3-(4-(2-(4-Fluorophenyl) ethoxy)phenyl)propyl) furan-2-carboxylic acid], WS070117 [O2', O3', O5'-tri-acetyl-N6-(3-hydroxylaniline)adenosine], PT1 [2-Chloro-5-[[5-[[5-(4,5-Dimethyl-2-nitrophenyl)-2-furanyl] methylene]-4,5-dihydro-4-ox-o-2-thiazolyl]amino]benzoic acid] and salts thereof. Metformin (also known as Fortamet®, Glucophage®, Glumetza®, Riomet®) was previously used as a treatment for type II diabetes. Proguanil (also known as Paludrine®) is an example of an AMPK activator and has been used as a prophylactic antimalarial drug.

In embodiments, the diuretic is selected from the group consisting of thiazide, amiloride, and other diuretics.

In embodiments, the P2Y purinergic receptor antagonist is selected from the group consisting of suramin, clopidogrel, reactive blue 2, acid blue 129, acid blue 80, and pyridoxal-phosphate-6-azophenyl-2',4'-disulfonic acid (PPADS).

Examples

In Vivo Models

Rats were given tolvaptan to induce NDI. Tolvaptan binds to and blocks the vasopressin type 2 receptor (V2R) and renders the animals insensitive to vasopressin-induced anti diuresis. The efficacy of three compounds of Formula I were evaluated. Each rat was gavage fed with 10 mg/kg/day of tolvaptan in the carrier solution (1% hydroxypropylmethyl cellulose in water) for 3 days to prepare the NDI model. The drugs were added to the gavage feeding solution and delivered daily for 4 days (NDI-5001, 200 mg/kg/day; NDI-5033 or NDI-5037, 50 mg/kg/day). Control rats were sham gavage fed. The bar graph shows the response to the drugs expressed as the percent of the untreated, fully concentrating rats (basal, set to 100%). As shown in FIG. 1B, the tolvaptan successfully produced a situation of nephrogenic diabetes insipidus, reducing the urine osmolality to 10% of the normal animal. Both NDI-5001 and NDI-5037 showed efficacy, NDI-5033, improved urine concentrating ability to 75% of normal.

Figure 2A:
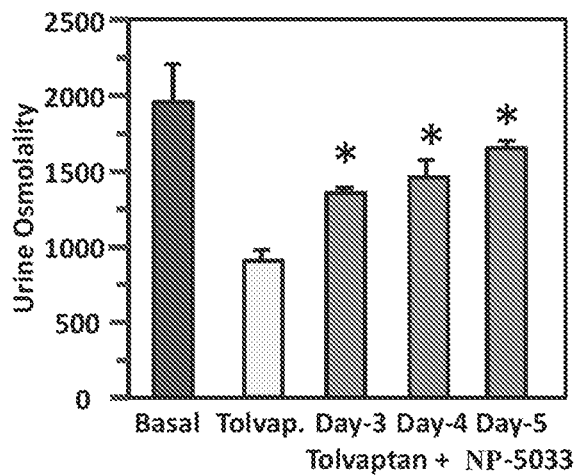
FIG. 2A shows data in a rat NDI model indicating compound of Formula I (NDI-5033) increases urine osmolality when dosed with NDI inducing agent tolvaptan.
Figure 2B:
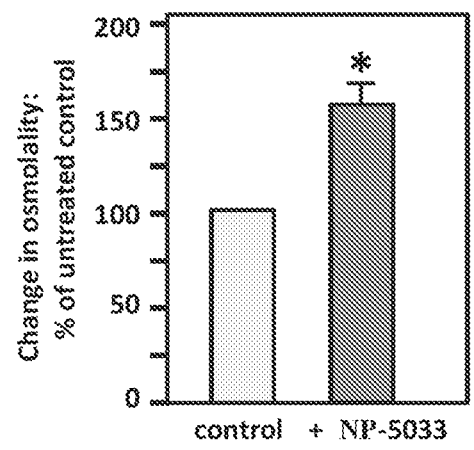
FIG. 2B shows efficacy of compound of Formula I (NDI-5033) in V2R knock-out mice.

NDI-5033 was tested to determine an initial time course and sustainability of the anti-diuretic response. Rats were given tolvaptan to initiate NDI. They were then fed 100 mg/kg/day with NDI-5033 for 3 days (FIG. 2A). Basal bar shows urine osmolality for fully concentrating rats. Tolvaptan shows minimal concentration in this model. Data indicates that NDI is effective within 24 hours of initial treatment and is sustained for 3 days. To ensure that the observed efficacy is not compromised by potential binding of NDI-5033 to V2R, NDI-5033 was given to mice in which the V2R was genetically knocked out yielding a genetic model of NDI (FIG. 2B). Control mice received no drug. NDI-5033 was given by injection to the mice and 24-hour urine collected and assessed for urine osmolality. NDI-5033 produced a 50% improvement in urine concentration.

Figure 3A:
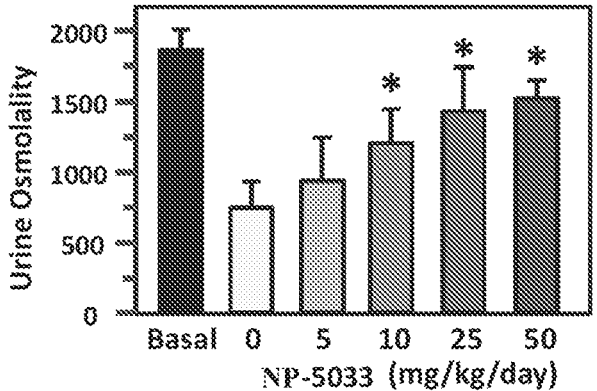
FIG. 3A shows efficacy of compound of Formula I (NDI-5033) in a dose response study in rat NDI model.
Figure 3B:
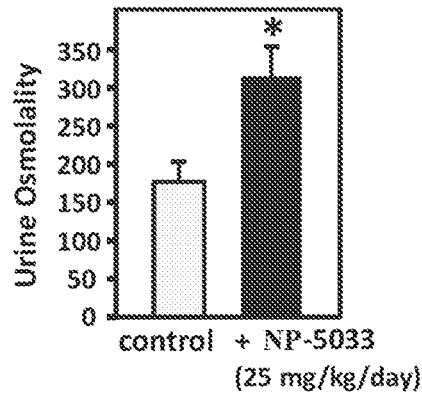
FIG. 3B shows efficacy of compound of Formula I (NDI-5033) in a genetic KO mouse NDI model.

Tolvaptan induced NDI rats were prepared and fed with doses of NDI-5033 from 0 to 100 mg/kg/day in a series of experiments. The drug NDI-5033 showed statistically significant improvements in urine concentrations at 10 mg/kg/day and above (FIG. 3A). To confirm the effectiveness of the 25 mg/kg/day dose, NDI-5033 was given to V2R knock-out NDI mice and 24-hour urines were assessed for urine osmolality (FIG. 3B). The osmolality was increased in NDI mice after treatment with 25 mg/kg/day of NDI-5033.

Figure 4A:
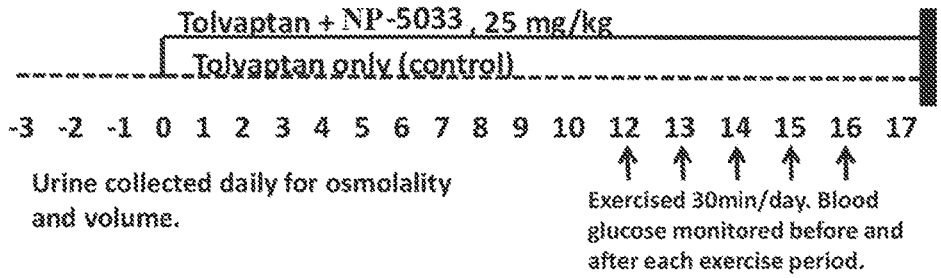
FIG. 4A illustrates a rat study conducted to evaluate hypoglycemia on chronic dosing with compound of Formula I.
Figure 4B:
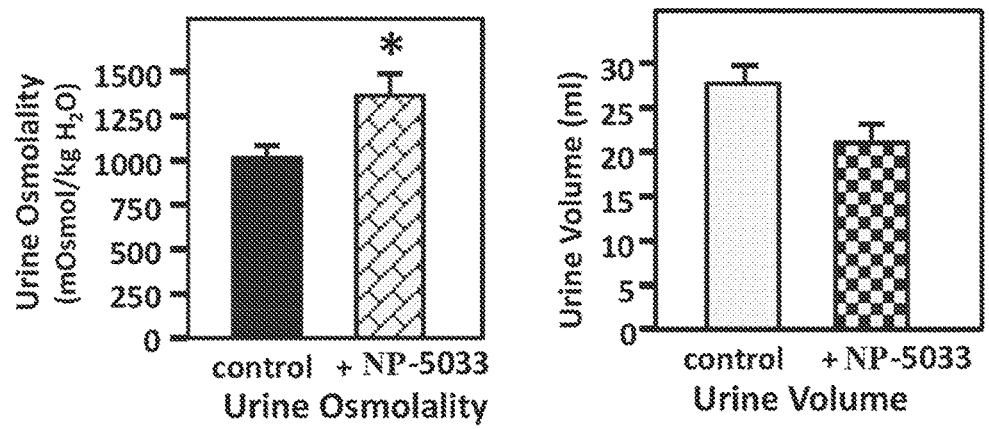
FIG. 4B shows data on the average urine osmolality and urine volumes in the NDI rats with or without dosing of compound of Formula I (NDI-5033).

An experiment was designed to approximate hypoglycemia in the tolvaptan-treated rat NDI model to look for hypoglycemia. A timeline for the experiment is illustrated in FIG. 4A. The rats were given tolvaptan beginning Day negative 3. On Day zero half of the rats started to receive 25 mg/kg/day of NDI-5033. After observing an improvement in the urine concentration, the animals were exercised daily for 5 days. Food was removed from the animals and NDI-5033 was given, then 4 hours later rats were subjected to 30 minutes of treadmill running. Blood glucose measurements were taken before and after the bout of exercise. Food was restored. The process was repeated daily for 5 days. The average urine osmolality and urine volumes in the NDI rats not receiving NDI-5033 (control) or receiving 25 mg/kg/day NDI-5033 is shown in FIG. 4B. Urine osmolality was increased (p<0.05) and urine volume decreased (p<0.07) upon drug treatment.

Figure 4C:
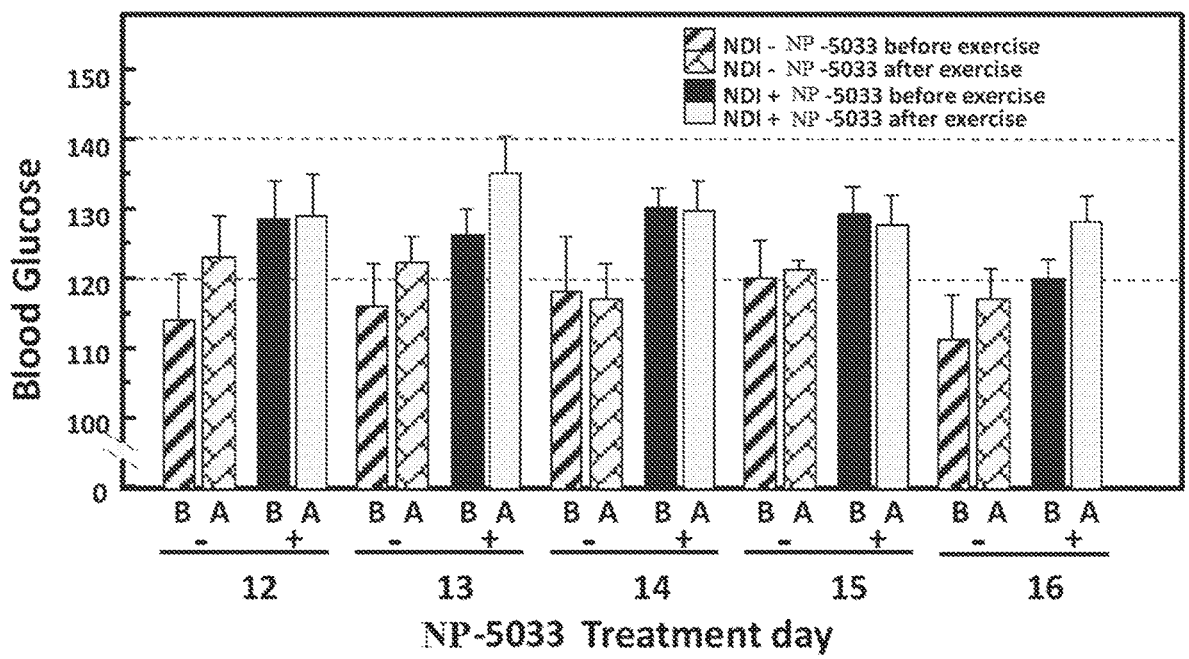
FIG. 4C shows data indicating exercised rats receiving compound of Formula I (NDI-5033) do not experience hypoglycemia. B=before and A=after exercise; −=no NDI-5033 and +=receiving NDI-5033; lines show normal range of blood glucose for rats.

FIG. 4C shows the blood glucose values for rats that were exercised. For each day, patterned bars are from rats not receiving NDI-5033. The leftmost bar (diagonal) is before and to the right 10 is after exercise. The next two bars show blood glucose values for rats receiving NDI-5033. Solid black is before and solid white is after exercise.

There is no statistical difference in either group comparing before and after exercise on any of the exercise days. All blood glucoses are within the normal range for rats designated by dashed lines at the bottom and top of the normal range. There was no evidence of hypoglycemia.

The invention claimed is:

1. A method for treating nephrogenic diabetes insipidus in a subject in need thereof, wherein the method comprises administering to the subject a therapeutically effective amount of a pharmaceutical composition comprising a pharmaceutically acceptable excipient and 1,1'-(dodecane-1,12-diyl)bis(cyclopropane-1-carboxamide) of the following structure:

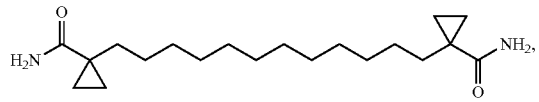 [SMILES: NC(=O)C1(CCCCCCCCCCCCC2(C(N)=O)CC2)CC1]

or a pharmaceutically acceptable salt thereof.

2. The method of claim 1, wherein the nephrogenic diabetes insipidus is acquired nephrogenic diabetes insipidus.

3. The method of claim 1, wherein the nephrogenic diabetes insipidus is congenital nephrogenic diabetes insipidus.

4. The method of claim 1, wherein the nephrogenic diabetes insipidus is induced by lithium therapy.

5. The method of claim 1, wherein the subject has at least one symptom of nephrogenic diabetes insipidus selected from the group consisting of the production of large quantities of dilute urine, excessive thirst, and excessive urination, or a combination thereof.

6. The method of claim 1, wherein the administering to the subject results in a reduction in the volume of urination in the subject to less than 20 L/day.

7. The method of claim 1, wherein the administering to the subject results in a reduction in the volume of urination in the subject to less than 15 L/day.

8. The method of claim 1, wherein the administering to the subject results in a reduction in the volume of urination in the subject to less than 10 L/day.

9. The method of claim 1, wherein the administering to the subject results in a reduction in the volume of urination in the subject to less than 5 L/day.

10. The method of claim 1, wherein the administering to the subject results in a reduction of the daily volume of urination in the subject by about 50%.

11. The method of claim 1, wherein the administering to the subject results in a reduction of the daily volume of urination in the subject by about 40%.

12. The method of claim 1, wherein the administering to the subject results in a reduction of the daily volume of urination in the subject by about 30%.

13. The method of claim 1, wherein the administering to the subject results in a reduction of the daily volume of urination in the subject by about 20%.

14. The method of claim 1, wherein the administering to the subject results in a reduction in the daily frequency of urination in the subject by about 50%.

15. The method of claim 1, wherein the administering to the subject results in a reduction in the daily frequency of urination in the subject by about 40%.

16. The method of claim 1, wherein the administering to the subject results in a reduction in the daily frequency of urination in the subject by about 30%.

17. The method of claim 1, wherein the administering to the subject results in a reduction in the daily frequency of urination in the subject by about 20%.

18. The method of claim 1, wherein the administering to the subject results in an increase in the daily urine osmolality in the subject by about 50%.

19. The method of claim 1, wherein the administering to the subject results in an increase in the daily urine osmolality in the subject by about 40%.

20. The method of claim 1, wherein the administering to the subject results in an increase in the daily urine osmolality in the subject by about 30%.

21. The method of claim 1, wherein the administering to the subject results in an increase in the daily urine osmolality in the subject by about 20%.

22. The method of claim 1, wherein the administering to the subject results in a urine osmolality in the subject greater than 125 mOsm/kg.

23. The method of claim 1, wherein the administering to the subject results in a urine osmolality in the subject greater than 150 mOsm/kg.

24. The method of claim 1, wherein the administering to the subject results in a urine osmolality in the subject greater than 200 mOsm/kg.

25. The method of claim 1, wherein:
(a) the administering to the subject does not alter blood sugar levels in the subject; or
(b) the administering to the subject does not induce hypoglycemia in a fasting condition in the subject.

26. The method of claim 1, wherein the administering to the subject does not result in gastrointestinal distress in the subject.

27. The method of claim 1, wherein the subject is an adult.

28. The method of claim 1, wherein the subject is a child.

29. The method of claim 1, wherein the pharmaceutical composition is administered to the subject orally.

30. The method of claim 1, wherein the pharmaceutical composition is a liquid composition.

31. The method of claim 1, wherein:
(a) the pharmaceutical composition is administered to the subject orally; and
(b) the pharmaceutical composition is a solid composition.

32. The method of claim 1, wherein:
(a) the pharmaceutical composition is administered to the subject daily; and
(b) the pharmaceutical composition comprises a therapeutically effective amount of 1,1'-(dodecane-1,12-diyl)bis(cyclopropane-1-carboxamide) in a range of about 5 mg to about 3,000 mg.

33. The method of claim 1, wherein the pharmaceutical composition comprises a therapeutically effective amount of 1,1'-(dodecane-1,12-diyl)bis(cyclopropane-1-carboxamide) in a range of about 10 mg to about 800 mg.

34. The method of claim 1, wherein the method further comprises administering to the subject a therapeutically effective amount of a second active agent.

35. The method of claim 34, wherein the second active agent is selected from the group consisting of an adenosine monophosphate-activated protein kinase activator, a cyclic guanosine monophosphate-specific phosphodiesterase inhibitor, a diuretic, and a P2Y purinergic receptor antagonist.

36. The method of claim 34, wherein the second active agent is lithium.

37. A method for treating nephrogenic diabetes insipidus in a subject in need thereof, wherein the method comprises administering to the subject a therapeutically effective amount of a pharmaceutical composition comprising a pharmaceutically acceptable excipient and 1,1'-(dodecane-1,12-diyl)bis(cyclopropane-1-carboxylic acid) of the following structure:

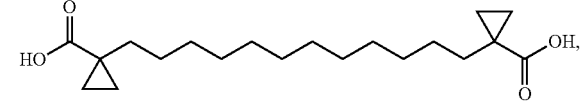 [SMILES: O=C(O)C1(CCCCCCCCCCCCC2(C(=O)O)CC2)CC1]

or a pharmaceutically acceptable salt thereof.

38. The method of claim 37, wherein the nephrogenic diabetes insipidus is acquired nephrogenic diabetes insipidus.

39. The method of claim 37, wherein the nephrogenic diabetes insipidus is congenital nephrogenic diabetes insipidus.

40. The method of claim 37, wherein the nephrogenic diabetes insipidus is induced by lithium therapy.

41. The method of claim 37, wherein the subject has at least one symptom of nephrogenic diabetes insipidus selected from the group consisting of the production of large quantities of dilute urine, excessive thirst, and excessive urination, or a combination thereof.

42. The method of claim 37, wherein the administering to the subject results in a reduction in the volume of urination in the subject to less than 20 L/day.

43. The method of claim 37, wherein the administering to the subject results in a reduction in the volume of urination in the subject to less than 15 L/day.

44. The method of claim 37, wherein the administering to the subject results in a reduction in the volume of urination in the subject to less than 10 L/day.

45. The method of claim 37, wherein the administering to the subject results in a reduction in the volume of urination in the subject to less than 5 L/day.

46. The method of claim 37, wherein the administering to the subject results in a reduction of the daily volume of urination in the subject by about 50%.

47. The method of claim 37, wherein the administering to the subject results in a reduction of the daily volume of urination in the subject by about 40%.

48. The method of claim 37, wherein the administering to the subject results in a reduction of the daily volume of urination in the subject by about 30%.

49. The method of claim 37, wherein the administering to the subject results in a reduction of the daily volume of urination in the subject by about 20%.

50. The method of claim 37, wherein the administering to the subject results in a reduction in the daily frequency of urination in the subject by about 50%.

51. The method of claim 37, wherein the administering to the subject results in a reduction in the daily frequency of urination in the subject by about 40%.

52. The method of claim 37, wherein the administering to the subject results in a reduction in the daily frequency of urination in the subject by about 30%.

53. The method of claim 37, wherein the administering to the subject results in a reduction in the daily frequency of urination in the subject by about 20%.

54. The method of claim 37, wherein the administering to the subject results in an increase in the daily urine osmolality in the subject by about 50%.

55. The method of claim 37, wherein the administering to the subject results in an increase in the daily urine osmolality in the subject by about 40%.

56. The method of claim 37, wherein the administering to the subject results in an increase in the daily urine osmolality in the subject by about 30%.

57. The method of claim 37, wherein the administering to the subject results in an increase in the daily urine osmolality in the subject by about 20%.

58. The method of claim 37, wherein the administering to the subject results in a urine osmolality in the subject greater than 125 mOsm/kg.

59. The method of claim 37, wherein the administering to the subject results in a urine osmolality in the subject greater than 150 mOsm/kg.

60. The method of claim 37, wherein the administering to the subject results in a urine osmolality in the subject greater than 200 mOsm/kg.

61. The method of claim 37, wherein:
(a) the administering to the subject does not alter blood sugar levels in the subject; or
(b) the administering to the subject does not induce hypoglycemia in a fasting condition in the subject.

62. The method of claim 37, wherein the administering to the subject does not result in gastrointestinal distress in the subject.

63. The method of claim 37, wherein the subject is an adult.

64. The method of claim 37, wherein the subject is a child.

65. The method of claim 37, wherein the pharmaceutical composition is administered to the subject orally.

66. The method of claim 37, wherein the pharmaceutical composition is a liquid composition.

67. The method of claim 37, wherein:
(a) the pharmaceutical composition is administered to the subject orally; and
(b) the pharmaceutical composition is a solid composition.

68. The method of claim 37, wherein:
(a) the pharmaceutical composition is administered to the subject daily; and
(b) the pharmaceutical composition comprises a therapeutically effective amount of 1,1'-(dodecane-1,12-diyl)bis(cyclopropane-1-carboxylic acid) in a range of about 5 mg to about 3,000 mg.

69. The method of claim 37, wherein the pharmaceutical composition comprises a therapeutically effective amount of 1,1'-(dodecane-1,12-diyl)bis(cyclopropane-1-carboxamide) in a range of about 10 mg to about 800 mg.

70. The method of claim 37, wherein the method further comprises administering to the subject a therapeutically effective amount of a second active agent.

71. The method of claim 70, wherein the second active agent is selected from the group consisting of an adenosine monophosphate-activated protein kinase activator, a cyclic guanosine monophosphate-specific phosphodiesterase inhibitor, a diuretic, and a P2Y purinergic receptor antagonist.

72. The method of claim 70, wherein the second active agent is lithium.

* * * * *